United States Patent [19]

Griffith

[11] Patent Number: 4,871,872
[45] Date of Patent: Oct. 3, 1989

[54] 2-[(2-AMINOACETYL)AMINO]ACETAMIDE DERIVATIVES

[75] Inventor: Ronald C. Griffith, Pittsford, N.Y.

[73] Assignee: Fisons Corporation, Rochester, N.Y.

[21] Appl. No.: 145,866

[22] Filed: Jan. 20, 1988

[51] Int. Cl.[4] ............................................. C07C 103/50
[52] U.S. Cl. ..................................... 564/157; 564/143; 564/155
[58] Field of Search ................. 564/155, 157; 514/616

[56] References Cited

U.S. PATENT DOCUMENTS 3,910,871 10/1975 Lindberg et al. .................... 564/155
4,537,781 8/1985 Darling ................................ 564/155

FOREIGN PATENT DOCUMENTS 955508 3/1957 Fed. Rep. of Germany .
343388 11/1960 Switzerland .
1420067 1/1976 United Kingdom ................ 564/157

OTHER PUBLICATIONS

CA 64,14162f.
CA 73,25044n.
CA 77,19586g.
CA 85,5705y.
CA 96,19744z.

Primary Examiner—Richard L. Raymond
Assistant Examiner—Susan P. Treanor
Attorney, Agent, or Firm—Seidel, Gonda, Lavorgna & Monaco

[57] ABSTRACT

Compounds are provided of the following general structure:

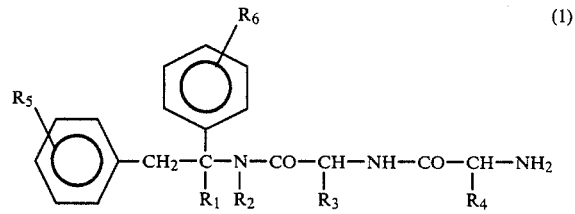

wherein $R_1$, $R_2$, $R_3$ and $R_4$ are hydrogen or methyl and where $R_5$ and $R_6$ are independently selected from hydrogen or fluorine.

These are useful for providing antiepileptic activity.

6 Claims, No Drawings

2-[(2-AMINOACETYL)AMINO]ACETAMIDE DERIVATIVES

SUMMARY OF THE INVENTION

Novel substituted 2-[(2-aminoacetyl)amino]acetamide derivatives have been prepared and found to possess useful antiepileptic activity.

GENERAL DESCRIPTION

This invention relates to novel 2-[(2-aminoacetyl)amino]acetamide compounds of the following general structure (1):

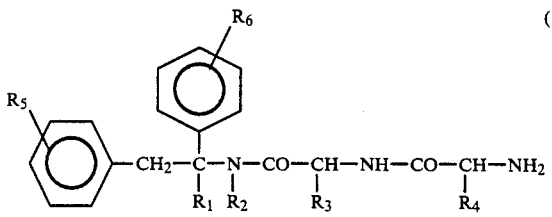

wherein $R_1$, $R_2$, $R_3$ and $R_4$ are hydrogen or methyl and where $R_5$ and $R_6$ are independently selected from hydrogen or fluorine.

This invention also relates to diastereomeric and optically resolved forms and to pharmaceutically acceptable acid addition salts of the compounds of general formula (1).

Compounds of this invention possess useful pharmaceutical properties. In particular they possess antiepileptic properties.

DETAILED DESCRIPTION

The 2-[(2-aminoacetyl)amino]acetamides of general formula (1) as described fully above are conveniently prepared by suitable amide bond forming reactions from the corresponding amine intermediates of general formula (2):

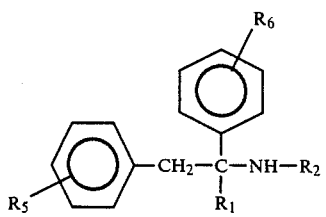

where $R_1$ and $R_2$ are taken to be hydrogen or methyl and $R_5$ and $R_6$ are hydrogen or fluorine and optical isomers thereof. Some of the amines of general formula (2) are known compounds and may be purchased commercially or conveniently prepared by suitable modifications of the reported procedures. Some of the amines (2) are not known, but are prepared by similar procedures. The preparation of the non-commercially available amines of general formula (2) is described in the "Preparation of Intermediates" Section.

Many amide bond forming reactions may in principle be utilized for the conversion of the amines of general formula (2) to the amides of general formula (1).

The preferred method consists of direct coupling of commercially available suitably protected amino acid derivatives of formula (3):

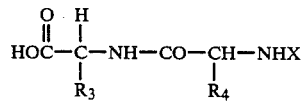

where $R_3$ and $R_4$ are hydrogen or methyl and where X is a urethane protecting group preferably benzyloxycarbonyl (CBZ) or t-butyloxycarbonyl (BOC), with an amine of general formula (2), in an inert solvent in the presence of a coupling reagent such as dicyclohexylcarbodiimide with or without 1-hydroxybenzotriazole or other additives to provide coupled products of general formula (4):

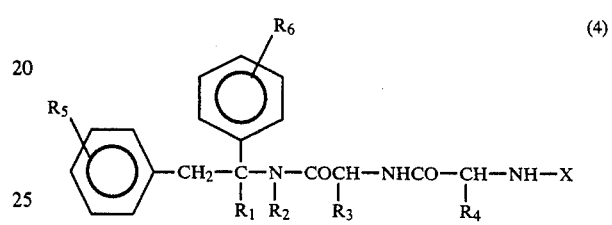

The protecting groups X, are then readily removed by either catalytic hydrogenation for the CBZ groups or treatment with an acid such as trifluoroacetic or hydrochloric acid for the BOC group to provide the compounds of general formula (1).

The compounds of general formula (1) possess asymmetric centers, and therefore optical isomers and diastereomeric forms are possible. Such compounds are conveniently prepared from optically active amines of formula (2) and/or optically active (3) by the methods described above.

The compounds of general formula (1) are basic compounds and may be used as such or pharmaceutically acceptable acid addition salts may be prepared by treatment with various inorganic or organic acids, such as hydrochloric, hydrobromic, sulfuric, phosphoric, acetic, lactic, succinic, fumaric, malic, maleic, tartaric, citric, benzoic, methansulfonic or carbonic acids.

The compounds of general formula (1) possess useful pharmaceutical properties. In particular they possess useful antiepileptic properties. These activities were assessed by standard methods. Antiepileptic activity was measured by assessing a compound's ability to prevent the hind limb tonic extension component of the seizure in groups of mice induced by maximal electroshock (MES) after oral or intraperitoneal administration according to the procedures of the Epilepsy Branch, NINCDS are published by R. J. Porter, et al., *Cleve. Clin. Quarter* 1984, 51, 293, and compared to the standard agents dilantin and phenobarbital. Activities ($ED_{50}$'s) in the range of 10-400 m/k after oral administration in this assay system were obtained.

The following non-limiting illustrations and examples are provided to exemplify the preparation of the intermediate amines of formula (2) and their conversion to the novel compounds of general formula (1).

PREPARATION OF INTERMEDIATES

Illustration 1

Preparation of 1,2-Diphenyl-2-propylamine hydrochloride

This compound was prepared by suitable modification of the procedures described by *Christol, Bull Soc. Chim. Fr*, 1963, 4, 877, and Ho and Smith, *Tetrahedron*, 1970, 26, 4277 as follows: To a suspension of sodium cyanide (34.3 g, 0.7 mol) in 500 ml of glacial acetic acid and 100 ml of n-butylether at 0° C. was added protionwise 200 ml of concentrated sulfuric acid. The ice bath was removed and a solution of 1,2-diphenyl-2-propanol (106 g, 0.5 m) in 100 ml of n-butylether was added dropwise over a period of 2 hours, then the mixture stirred for 48 hours. The mixture was poured into 1000 ml of ice, and extracted with chloroform. The extracts were washed with water, dried and evaporated to a solid residue which was stirred with hexane (500 ml), filtered and dried to give 85.35 g (72% yield) of N-formyl-1,2-diphenyl-2-propylamine, mp 97°–99° C. This was suspended in 1 L of 10% HCl and heated to reflux for 2.5 hours. After cooling in air for 1 hour then in an ice bath for 30 minutes, the white solid which had crystallized was collected by filtration and vacuum dried to give 85.9 g (97% yield) of 1,2-diphenyl-2-propylamine hydrochloride, mp 175°–178° C.

Illustration 2

Preparation of 1,2-bis-(4-fluorophenyl)-2-propylamine hydrochloride

By procedures essentially the same as those described in Illustration 1, and by substituting 1,2-bis(4-fluorophenyl)-2-propanol (prepared by the reaction of 4-fluorobenzyl magnesium chloride and 4'-fluoroacetophenone) for 1,2-diphenyl-2-propanol; the corresponding 1,2-bis(4-fluorophenyl)-2-propylamine hydrochloride, mp 188°–189° C., is prepared.

Illustration 3

Preparation of (−)-1,2-diphenyl-2-propylamine

Racemic 1,2-diphenyl-2-propylamine (86 g, 0.4 mol) was dissolved in 0.5 L 95% ethanol, heated to near reflux and added to a solution of (−)-dibenzoyltartaric acid monohydrate (151.9 g, 0.4 mol) in 0.5 L 95% ethanol also at reflux. A white solid crystallized immediately. The mixture was refluxed for 5 minutes, then allowed to cool to ambient temperature. The solid was collected by filtration and dried to give 86.2 g, $[\alpha]_D = 94.2°$ (C=0.5, CH$_3$OH). The filtrate was saved. The solid was suspended in 0.9 L of 95% ethanol, stirred and heated to reflux for 1 hour, allowed to cool to ambient temperature and the white solid collected by filtration and vacuum dried at 80° C. for 8 hours to give 60.2 g of (−)-1,2-diphenyl-2-propylamine (−)-dibenzoyl tartrate, mp 194°–195° C. $[\alpha]_D = -96.0°$ (C=0.5, CH$_3$OH). 5.0 g of this salt was dissolved in 250 ml CHCl$_3$ and 200 ml 5% NH$_4$OH shaken vigorously, the layers separated and the organic phase washed with 3×200 ml 5% NH$_4$OH, 2×200 ml H$_2$O and dried over MgSO$_4$. The solvent was evaporated to give 1.75 g of (−)-1,2-diphenyl-2-propylamine as an oil. The maleate salt was prepared by dissolving this oil in 25 ml of ethyl acetate and adding the solution to a hot solution of maleic acid (1.02 g, 8.87 mmol) in 50 ml of 3/1 ethyl acetate/isopropanol. Upon cooling a white solid crystallized, which was collected by filtration and vacuum dried to give 2.05 g of (−)-1,2-diphenyl-2-propylamine maleate, mp 176°–177° C., $[\alpha]_D = -27.4°$ (C=1, CH$_3$OH).

Illustration 4

Preparation of (+)-1,2-Diphenyl-2-propylamine

The filtrate residue which was saved in Illustration 3, was treated with 1 L CHCl$_3$ and 0.9 L 5% NH$_4$OH, shaken vigorously, the layers separated and the organic phase washed with 4×800 ml 5% NH$_4$OH and 2×500 ml H$_2$O, then dried over MgSO$_4$ and evaporated to an oil 32.3 g, which is enriched in (+)-1,2-diphenyl-2-propylamine. This oil (32.3 g, 0.153 mol) was dissolved in 200 ml hot 95% ethanol and added to a stirred solution of (+)-dibenzoyl tartaric acid monohydrate (57.55 g, 0.153 mol) in 600 ml of refluxing 95% ethanol. A white solid crystallized immediately, which was stirred at reflux for 5 minutes, then allowed to cool to ambient temperature. The solid was collected by filtration and vacuum dried at 80° C. for 8 hours to give 71.6 g of (+)-1,2-diphenyl-2-propylamine (+)-dibenzoyltartrate, mp 197°–198° C., $[\alpha]_D = +95.8°$ (C=0.5, CH$_3$OH). 5.0 g of this salt use dissolved in 250 ml CHCl$_3$ and 200 ml 5% NH$_4$OH, shaken vigorously, the layers separated and the organic phase washed with 3×200 ml 5% NH$_4$OH and 2×200 ml H$_2$O and dried over MgSO$_4$. The solvent was evaporated to give 1.75 g of (+)-1,2-diphenyl-2-propylamine as an oil. The maleate salt was prepared by dissolving this oil in 25 ml ethyl acetate and adding the solution to a hot solution of maleic acid (1.02 g, 8.78 mmole) in 50 ml 3/1 ethyl acetate/isopropanol. Upon cooling a white solid crystallized, which was collected by filtration and vacuum dried to give 2.06 g of (+)-1,2-diphenyl-2-propylamine maleate, mp 177°–178° C., $[\alpha]_D = +27.3°$ (C=1, CH$_3$OH).

Illustration 5

Preparation of N-methyl-1,2-diphenyl-2-propylamine hydrochloride

N-formyl-1,2-diphenyl-2-propylamine (23.6 g, 0.1 mol) was added to a stirred suspension of LiAlH$_4$ (15.0 g, 0.395 mol) in 1 L of dry tetrahydrofuran. After 2 hours the mixture was heated at 35° C. for 22 hours, then refluxed for 2 hours, and allowed to cool to room temperature. Water was added to decompose the excess LiAlH$_4$, and the mixture filtered to remove the solid salt. Evaporation of the solvent gave 23.0 g of the crude product as a yellow oil. This was dissolved in 180 ml of ethyl acetate and 20 ml of isopropanol and acidified with HCl gas. Upon standing a white solid crystallized which was collected by filtration and vacuum dried at 65° C. to give 21.7 g (84% of N-methyl-1,2-diphenyl-2-propylamine hydrochloride, mp 200°–201° C.

Illustration 6

Preparation of N-Methyl-1,2-diphenylethylamine

To a stirred two phase solution of 1,2-diphenylethylamine (30.0 g, 0.15 mol) in 300 ml of methylene chloride and 500 ml of water was added sodium carbonate (23.9 g, 0.225 mol) and the solution was cooled to 10° C. under nitrogen. Ethyl chloroformate (21.5 ml, 0.225 mol) was added dropwise over a one hour period. The reaction was warmed to ambient temperature and stirred at that temperature for 3 hours. The phases were separated and the aqueous phase was extracted with methylene chloride (75 ml). The combined methylene chloride extracts were washed with 1N HCl (200 ml), brine (200 ml), dried and evaporated to a white solid, 40.3 g. Recrystallization from cyclohexane gave N-carboethoxy-1,2-diphenylethylamine, mp 74°–75° C.

To a stirred suspension of lithium aluminum hydride (12.4 g, 0.032 mol) in 300 ml of tetrahydrofuran at 0° C. under nitrogen was added dropwise a solution of N-carboethoxy-1,2-diphenylethylamine (35.0 g, 0.13 mmol) in 200 ml of tetrahydrofuran. The mixture was heated to reflux for 8 hours. The mixture was cooled in an ice-water bath and water (13 ml), 15% NaOH (13 ml) and water (39 ml) were carefully added to the mixture. The mixture was warmed to ambient temperature and the precipitated salts were removed by filtration through celite. Removal of solvent gave N-methyl-1,2-diphenylethylamine, 26.8 g as a colorless oil.

Treatment of this oil with maleic acid in ethyl acetate and methanol gave N-methyl-1,2-diphenylethylamine maleate, mp 129°–131° C.

EXAMPLE 1

Preparation of
2-Glycinamido-N-(1,2-diphenyl-1-methylethyl)acetamide hydrochloride To a stirred solution of 1,2-diphenyl-2-propylamine (11.5 g, 0.055 mol) in 400 ml of chloroform under nitrogen was added N-CBZ-glycylgylcine (16.0 g, 0.060 m), and then a solution of dicyclohexylcarbodiimide (11.4 g, 0.055 mol) in 125 ml of chloroform and the mixture stirred for 72 hours. The precipitated solid was removed by filtration and the solvent evaporated. The residual oil was recrystallized from ethyl acetate (500 ml) and then methanol (500 ml) to give a white solid, 12.9 g. This was dissolved in methanol (200 ml) and acidified with HCl gas to give a white solid, 12.5 g. This was dissolved in 900 ml of methanol and 90 ml of 10% HCl, and hydrogenated at 40 spi in a Parr apparatus over 3.0 g of 10% Pd/c catalyst for 4 hours. The catalyst was removed by filtration, and the solvent evaporated to a white solid 6.5 g. This was dissolved in water (500 ml), basified with ice cold NaOH solution, and extracted with EtOAc (3×250 ml). The combined organic extracts were dried and evaporated to a white solid, 6.3 g. This was dissolved in isopropanol (250 ml) and ethyl acetate (150 ml) and acidified with HCl gas. Upon cooling a white solid crystallized, which after vacuum drying at 80° C. for 40 hours gave 5.3 g of 2-glycinamido-N-(1,2-diphenyl-1-methylethyl) acetamide, mp. 226°–228° C.

EXAMPLE 2

Preparation of
(2S)-2-Glycinamido-N-(1,2-diphenyl-1-methylethyl)-propanamide

By procedures essentially the same as those described in Example 1 and by substituting N-CBZ-glycyl-L-alanine for N-CBZ-glycylglycine the corresponding (2S)-2-glycinamido-N-(1,2-diphenyl-1-methylethyl)propanamide mp. 155°–156° C., was prepared.

EXAMPLE 3

Preparation of
2-(L-Alaninamido)-N-(1,2-diphenyl-methylethyl)acetamide

By procedures essentially the same as those described in Example 1 and by substituting N-CBZ-L-alanylglycine for N-CBZ-glycylglycine; the corresponding 2-(L-alaninamido)-N-(1,2-diphenyl-1-diphenyl-1-methylethyl)acetamide may be prepared.

EXAMPLE 4

Preparation of
(2S)-2-(L-alaninamido)-N-(1,2-diphenyl-1-methylethyl)propanamide

By procedures essentially the same as those described in Example 1 and by substituting N-CBZ-L-alanyl-L-alanine for N-CBZ-glycylglycine; the corresponding (2S)-2-(L-alaninamido)-N-(1,2-diphenyl-1-methylethyl)propanamide, mp. 161°–162° C., was prepared.

EXAMPLE 5

Preparation of
2-Glycinamido-N-[1,2-bis(4-fluorophenyl)-1-methylethyl]acetamide

To a stirred solution of 1,2-bis(4-fluorophenyl)-2-propylamine (8.47 g, 0.034 mol) in 200 ml of chloroform under nitrogen, was added N-CBZ-glycylglycine (9.13 g, 0.034 mol) and then a solution of dicyclohexylcarbodiimide (7.43 g, 0.036 mol) in 100 ml of chloroform and the mixture stirred for 72 hours. The precipitated solid was removed by filtration and the solvent evaporated. The residue was treated with ethylacetate (125 ml), filtered, an additional 250 ml of ethylacetate added and then washed with cold 1% HCl (150 ml), brine (200 ml), dried and the solvent evaporated. The residue was dissolved in 400 ml of methanol and 35 ml of 10% HCl and hydrogenated at 40 psi in a Parr apparatus over 3.0 g of 5% Pd/c catalyst for 3 hours. The catalyst was removed by filtration, solvent evaporated and the residue dissolved in water (300 ml) and chloroform (300 ml), basified to pH 11 with 50% NaOH, shaken and separated. The aqueous phase was extracted with chloroform (3×150 ml), and the combined organic phases were washed with water (2×200 ml), dried, and evaporated to a pale yellow oil. This oil was crystallized from cyclohexane (150 ml) and ethanol (5 ml); the solid obtained was recrystallized from hexane (150 ml) and ethanol (10 ml), and vacuum dried at 83° C. for 96 hours to give 3.64 g of 2-glycinamido-N-[1,2-bis(4-fluorophenyl)-1-methylethyl]acetamide, mp. 139°–140° C.

EXAMPLE 6

By procedures essentially the same as those described in Example 1 and substituting (−) or (+) 1,2-diphenyl-2-propylamine for 1,2-diphenyl-2-propylamino; the corresponding (−) or (+)-2-glycinamido-N-(1,2-diphenyl-1-methylethyl) acetamide hydrochlorides may be prepared.

EXAMPLE 7

By procedures essentially the same as those described in Example 1 and substituting N-methyl-1,2-diphenylethylamine or N-methyl-1,2-diphenyl-1-methylethylamine for 1,2-diphenyl-2-propyl-amine, the corresponding 2-glycinamido-N-methyl-N-(1,2-di-phenylethyl)acetamide hydrochloride or 2-glycinamido-N-methyl-N-(1,2-methylethyl)acetamide hydrochloride may be prepared.

I claim:

1. A compound having the formula:

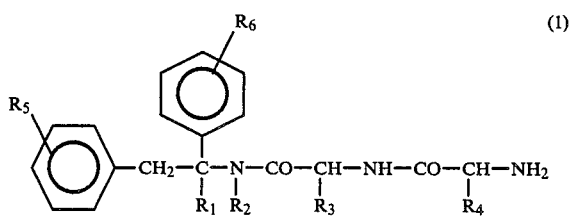

(1)

wherein $R_1$, $R_2$, $R_3$ and $R_4$ are hydrogen or methyl and where $R_5$ and $R_6$ are independently selected from hydrogen or fluorine.

2. A compound according to claim 1 wherein the compound is 2-glycinamido-N-(1,2-diphenyl-1-methylethyl) acetamide hydrochloride.

3. A compound according to claim 1 wherein the compound is (2S)-2-glycinamido-N-(1,2-diphenyl-1-methylethyl)propanamide.

4. A compound according to claim 1 wherein the compound is 2-(L-alaninamido)-N-(1,2-diphenyl-methylethyl) acetamide.

5. A compound according to claim 1 wherein the compound is (2S)-2-(L-alaninamido)-N-(1,2-diphenyl-1-methylethyl)propanamide.

6. A compound according to claim 1 wherein the compound is 2-glycinamido-N-[1,2-bis(4-fluorophenyl)-1-methylethyl]acetamide.

* * * * *